US010591499B2

(12) United States Patent
Littmann et al.

(10) Patent No.: US 10,591,499 B2
(45) Date of Patent: Mar. 17, 2020

(54) METHOD FOR OPERATING AN AUTOMATED ANALYZER

(71) Applicant: Endress+Hauser Conducta GmbH+Co. KG, Gerlingen (DE)

(72) Inventors: Michael Littmann, Bietigheim-Bissingen (DE); Ulrich Rottensteiner, Stuttgart (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 104 days.

(21) Appl. No.: 15/473,881

(22) Filed: Mar. 30, 2017

(65) Prior Publication Data

US 2017/0285051 A1   Oct. 5, 2017

(30) Foreign Application Priority Data

Mar. 30, 2016   (DE) .................. 10 2016 105 773

(51) Int. Cl.
   *G01N 35/00*   (2006.01)
   *G01N 35/10*   (2006.01)
   *G01N 35/04*   (2006.01)

(52) U.S. Cl.
   CPC .... *G01N 35/00693* (2013.01); *G01N 35/1004* (2013.01); *G01N 35/1097* (2013.01); *G01N 2035/0437* (2013.01)

(58) Field of Classification Search
   None
   See application file for complete search history.

(56) References Cited

U.S. PATENT DOCUMENTS

| | | | | | |
|---|---|---|---|---|---|
| 5,817,954 A | * | 10/1998 | Kahng | ............... | G01N 33/1886 73/863.84 |
| 2011/0027893 A1 | * | 2/2011 | Kathe | ............... | G01N 33/1806 436/62 |
| 2017/0212091 A1 | * | 7/2017 | Feng | ............... | G01N 33/18 |

FOREIGN PATENT DOCUMENTS

| | | | |
|---|---|---|---|
| CN | 101294907 B | * | 12/2010 |
| CN | 202928848 U | | 5/2013 |
| CN | 103353513 A | * | 10/2013 |
| CN | 103353513 A | | 10/2013 |
| DE | 69524732 T2 | | 11/2002 |
| DE | 10227032 A1 | | 11/2003 |
| DE | 10222822 A1 | | 12/2003 |
| DE | 102009029305 A1 | | 3/2011 |

OTHER PUBLICATIONS

English translation of CN 103353513 date (Oct. 2013).*
Abstract of CN101294907 (Dec. 2010).*
Search Report for German Patent Application No. 10 2016 105 773.8, German Patent Office, dated Feb. 25, 2017, 7 pp.

* cited by examiner

*Primary Examiner* — Kathryn Wright
(74) *Attorney, Agent, or Firm* — Christopher R. Powers; PatServe

(57) ABSTRACT

The disclosure concerns a method for operating an automated analyzer, including transporting a liquid containing a plurality of particles into a chamber, such as a reactor chamber and/or measuring cell chamber of the analyzer, introducing a gas or gas mixture, for example, air into the chamber, such as through the liquid present in the chamber so that the particles in the liquid are stirred up, and subsequently draining at least part of the liquid from the chamber through a fluid line ending in the chamber and an open valve arranged in the fluid line.

15 Claims, 1 Drawing Sheet

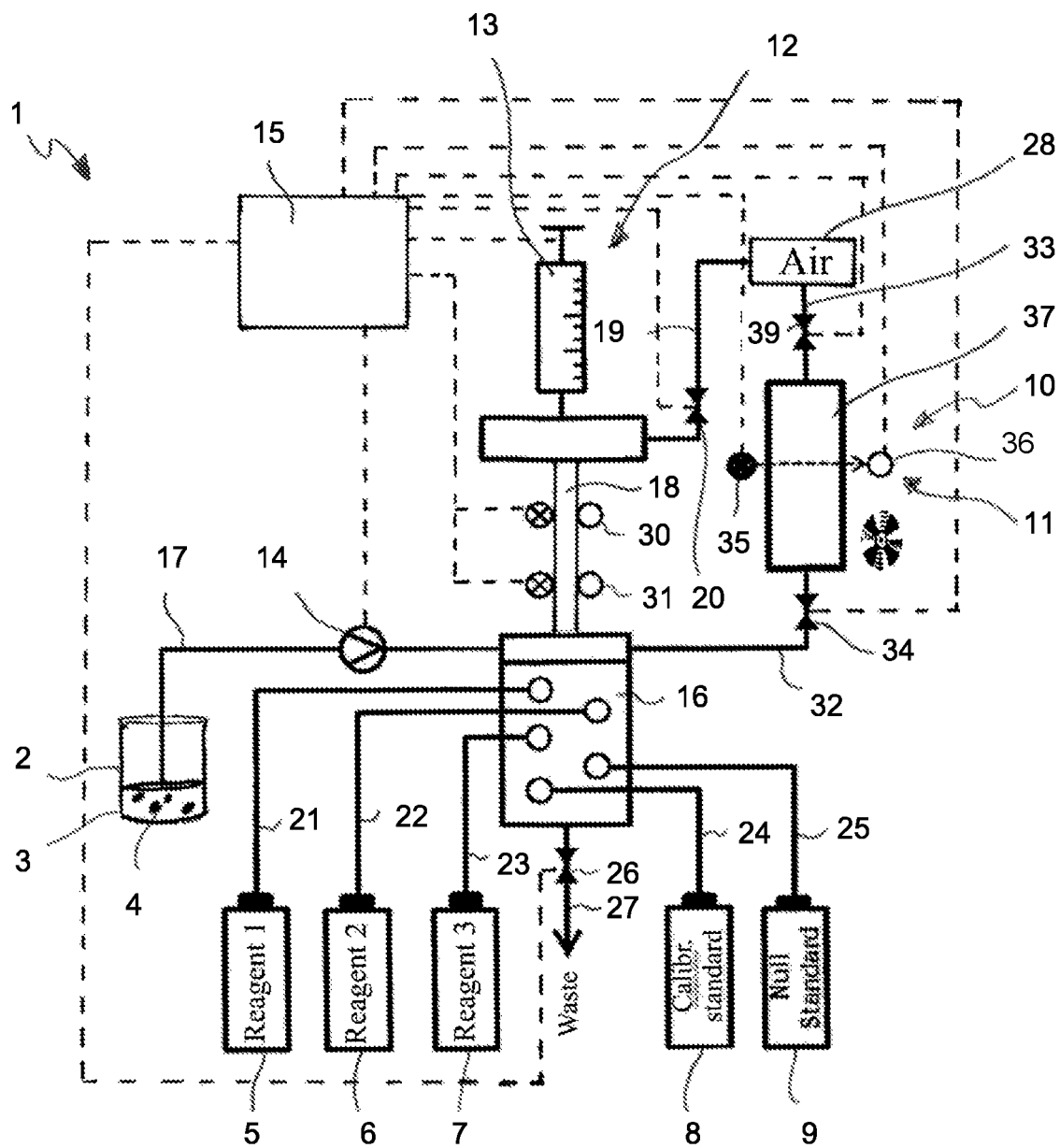

METHOD FOR OPERATING AN AUTOMATED ANALYZER

CROSS-REFERENCE TO RELATED APPLICATION

The present application is related to and claims the priority benefit of German Patent Application No. 10 2016 105 773.8, filed on Mar. 30, 2016, the entire contents of which are incorporated herein by reference.

TECHNICAL FIELD

The invention relates to a method for operating an automated analyzer for determining a parameter of a liquid sample, and an analyzer that is designed to automatically execute the method.

BACKGROUND

In process metrology, e.g., in chemical, biotechnological, pharmaceutical, and food industry processes, as well as in environmental metrology, such automated analyzers are used to determine a measurand in a liquid sample. Such analyzers may, for example, be used for the monitoring and optimization of the cleaning performance in a sewage treatment plant, for monitoring drinking water, or for monitoring quality of foodstuffs. For example, the proportion of a specific substance, which is also termed an analyte, in a sample liquid such as a liquid mixture, emulsion, suspension, gas, or gas mixture is measured and monitored. Analytes may, for example, be ions such as ammonium, phosphate, silicate, nitrate, calcium, sodium, or chloride, or biological or biochemical compounds, e.g., hormones, or even micro-organisms. Other parameters that are determined using analyzers in process metrology, for example, in the field of monitoring water, are cumulative parameters such as the total organic carbon (TOC), total nitrogen (TM), total phosphorus (TP), or the chemical oxygen demand (COD). Analyzers may, for example, be designed as cabinet devices or buoys.

The sample to be analyzed is often treated inside analyzers by adding one or more reagents, thus provoking a chemical reaction in the reaction mixture formed in this manner. The reagents are preferably selected in order to render the chemical reaction verifiable by physical methods, e.g., by optical measurements, by means of potentiometric or amperometric sensors, or through a conductivity measurement. By means of a measuring sensor, measured values of a measurand that is correlated with the actual analytical parameter (such as COD) to be determined is detected. The chemical reaction may, for example, cause a coloring or a change in color which may be detected using optical means. In such cases, the intensity of the color is a measure of the parameter to be determined. As the measurand correlated with the parameter to be determined, absorption or extinction of the treated sample may, for example, be ascertained by photometric means by feeding electromagnetic radiation, such as visible light, from a radiation source into the liquid sample, and receiving it with a suitable receiver after transmission through the liquid sample. The receiver generates a measurement signal, which depends upon the intensity of the received radiation, and from which the parameter to be determined can be derived for example, by means of a calibration function or table. The parameter value is generally derived by means of measuring electronics, such as a computer that is programmed to determine a measured value of the parameter from the measuring signal using the calibration function or table, and display, save, and/or output the measured value via an interface to a higher-level unit.

In order to use such methods of analysis in an automated way, e.g., in the industrial sector or for monitoring a sewage treatment plant or a body of water outdoors, it is desirable to provide an analyzer that automatically executes the required analytical processes. In addition to sufficient measuring precision, the most important requirements for such an analyzer are robustness, ease of use, low maintenance requirements, and the guarantee of sufficient occupational and environmental safety.

Automatic analyzers are known in the state of the art. For example, DE 102 22 822 A1, DE 102 27 032 A1, and DE 10 2009 029305 A1 disclose generic analyzers for determining one or more parameters of a sample liquid. Such analyzers are each designed as a cabinet device containing measuring and control electronics, a supply tank for reagents, standard solutions, and cleaning liquids, pumps to feed and dose the liquid sample and the reagent or reagents into a measuring cell, and a measuring sensor for optical measurements of the sample exposed to the reagent or reagents in the measuring cell, or a reaction mixture formed therefrom. Controlled by the measuring and control electronics, the reagents, standard solutions, or cleaning liquids are conveyed from the supply tanks and transported into the measuring cell. Correspondingly, used liquid is transferred from the measuring cell into a waste container.

Particularly in applications in the fields of environmental analytics or water management, the sample liquid can contain a particle load to be monitored by means of an automated analyzer. The entrained particles can be filtered out of the sample liquid for example, when sampling from the measuring point so that the sample supplied to the analyzer for analysis is free of particles, and there is, accordingly, no danger of the fluid lines or valves of the analyzer becoming obstructed or blocked by any particles entrained by the sample. The chemical composition of the particle load of a sample liquid is, however, part of certain parameters like digestion parameters such as COD or TP, so that filtering out the particles from the sample before performing the analysis would significantly distort the analytical results. Generally, the sample liquid is therefore analyzed with the inclusion of its particle load. The liquid lines of the analyzer which come into contact with the sample liquid must be designed for this. In locations at which a high flow speed generally predominates, the probability of blockage by particles entrained in the sample liquid is less than at locations in which the sample liquid dwells for a long time where particles can settle. This is, in particular, the case in the measuring cell of the analyzer. The blocking of valves and fluid lines requires regular servicing measures and/or the regular exchange of valves and fluid lines.

BRIEF SUMMARY

It is, therefore, the object of the invention to present a method for operating an automated analyzer, and an analyzer designed to perform the method, in which the amount of maintenance is reduced that arises from valves and/or liquid lines becoming blocked due to an entrained particle load in the sample liquid.

This object is achieved by the method according to claim 1 and the analyzer according to claim 15. Further embodiments are listed in the dependent claims.

The method according to the invention for operating an automated analyzer comprises: transporting a liquid containing a plurality of particles into a chamber in particular, a reactor chamber and/or measuring cell chamber of the analyzer; introducing a gas or gas mixture in particular, air into the chamber in particular, through the liquid present in the chamber so that the particles in the liquid are stirred up; and subsequently draining at least part of the liquid from the chamber through a fluid line ending in the chamber and an open valve arranged in the fluid line.

The valve can be designed so that, when in an open state, it allows liquid or gas to be transported through the fluid line and, in a closed state, blocks the transportation of liquid or gas through the fluid line. If the liquid dwells for a long time in the chamber of the analyzer, at least a portion of the particles in the liquid settle. If the liquid were then to be drained through the valve, all of the settled particles would be flushed at the same time into the valve and would cause a blockage of the possibly narrow and/or angled valve seat within a short time. By introducing a gas or gas mixture according to the invention into the chamber, the particles in the liquid are stirred up and do not pass simultaneously through the narrow sections in the valve when draining. This significantly reduces the danger of blockage.

The liquid in a reactor or measuring cell of the analyzer has a particularly long dwell time. In one embodiment, the chamber is, therefore, a reactor chamber formed in a reactor of the analyzer and/or a measuring cell chamber formed in the measuring cell of the analyzer.

The gas or gas mixture is introduced below the level of the liquid into the chamber, so that the gas or gas mixture flows through the liquid.

The particle-containing liquid can, for example, be a sample liquid which is fed to the analyzer in order to determine a parameter of the sample liquid by means of the analyzer. The parameter can, for example, be a digestion parameter such as COD or TP. The method for operating the analyzer can comprise at least one rinsing step in which the sample liquid is transported from a sample recipient vessel through one or more fluid lines of the analyzer into the chamber, such as the measuring cell chamber, and then drained therefrom. In this rinsing step, the sample liquid is not treated with other reagents, but, rather, only rinsed through the fluid lines and chambers of the analyzer intended to receive liquid. The rinsing step may be repeated several times. After the liquid for rinsing purposes is transported into the analyzer chamber, which can, for example, be a reactor chamber and/or a measuring cell chamber as mentioned, first the gas or gas mixture is conducted into the chamber in order to stir up the particles contained in the liquid, and then at least part of the liquid is drained from the chamber through the fluid line and open valve.

Alternatively, the particle-containing liquid can be a reaction mixture that is formed from the sample liquid and at least one reagent added to the sample liquid. To ascertain the measured value of the parameter to be determined by the analyzer, the given volume of sample liquid is removed as a sample from the sample recipient vessel, and at least one reagent is added to form the reaction mixture. The sample and reagent can be mixed, and a chemical reaction such as chemical digestion in the reaction mixture can be performed in the chamber of the analyzer, wherein the chamber can, for example, be the aforementioned reactor chamber or the likewise aforementioned measuring cell chamber. Even after the conclusion of the chemical reaction, particles can remain in the reaction mixture, which settle over the dwell time of the reaction mixture in the chamber or measuring cell chamber. Advantageously, the gas or gas mixture is therefore introduced into the chamber before draining at least part of the reaction mixture from the chamber, in order to stir up the particles and accordingly prevent the narrow sections in the valve from being blocked.

The sequence of steps of introducing the gas or gas mixture and subsequently draining part of the liquid from the chamber can be repeated once or several times until the chamber has been completely drained.

The introduction of the gas or gas mixture can be concluded before draining at least part of the liquid. In this case, preferably between terminating the introduction of the gas or gas mixture and draining the at least part of the reaction mixture, there is a time span that is less than the time span required for the stirred-up particles to settle.

In an embodiment, the gas or gas mixture can be introduced in bursts, and/or the liquid for draining can be abruptly drawn from the chamber. This procedure counteracts an even flow and causes the particles to flow in a rather jumbled and random manner through the valve, which accordingly further reduces the danger of blocking.

In one embodiment of the method, the liquid can be transported into the chamber at a first delivery rate, and part of the liquid can be drained at a second delivery rate, wherein the second delivery rate is higher than the first delivery rate. The liquid can be transported into the chamber, and the liquid can be drained from the chamber, by means of two different pumps, or one and the same pump. The second delivery rate can, for example, be 2 to 10 times the first delivery rate.

The drainage of at least part of the liquid can comprise drawing off part of the liquid by means of a pump, wherein drawing is interrupted at least once and preferably several times. The aforementioned abrupt drawing of the liquid can be achieved in this manner.

In one embodiment of the method, the gas or gas mixture in particular air can, for example, be introduced into the chamber from a gas reservoir under an overpressure, e.g., from a compressed gas tank, via a fluid line ending in the chamber.

In an embodiment, the gas or gas mixture can be air, wherein the air is drawn by means of an analyzer pump from the atmosphere surrounding the analyzer, and introduced into the chamber by means of the pump via a fluid line ending in the chamber.

The liquid containing a plurality of particles can be transported, and the gas or gas mixture can be introduced into the chamber, by the same fluid line, for example.

In such an embodiment, the pump can be fluidically connected to the fluid line. To drain at least part of the liquid from the chamber, the part of the liquid can be transported by means of the pump from the chamber through the fluid line into a waste container.

The method can moreover comprise the detection of at least one measured value of a measurand, correlated to a parameter of the sample liquid, of a reaction mixture formed from a given volume of the sample liquid and at least one reagent, and the ascertainment of the parameter value using the detected measured value. The latter can, for example, be done using a calibration function and/or a table that assigns each of the measured values a sample liquid parameter value.

All of the method steps of the method according to the invention, and/or the above-described embodiments of the method, can be performed automatically by means of measuring and control electronics. The measuring and control electronics can comprise an electronic data processing device such as a computer or a measuring transducer that is programmed to control the opening and closing of the valve, the draining of the liquid and the introduction of the gas or gas mixture, the possibly available pump, and other functions of the analyzer, in order to perform the method described here.

The present disclosure also comprises an analyzer for performing the method according to one of the above-described embodiments. The analyzer comprises: measuring and control electronics; a chamber formed in the analyzer in particular, a measuring cell chamber and/or reactor chamber; at least one fluid line that ends in the chamber and in which a valve is arranged that releases the transport of gas or liquid in an open state, and blocks in the transport of gas or liquid in a closed state; and a first fluid flow path that comprises a first valve device, by means of which the first fluid flow path can be optionally blocked or released, and that fluidically connects a sampling site or a sample recipient vessel to the chamber in particular, by the fluid line ending in the chamber; a pump arranged in the first fluid flow path; a second fluid flow path that comprises a second valve device, by means of which the second fluid flow path can be optionally blocked or released, and that fluidically connects the chamber to a gas reservoir in particular, to the atmosphere surrounding the analyzer; wherein the measuring and control electronics are programmed to control the analyzer in particular, the pump, valve, first valve device, and second valve device in order to perform the method according to one of the above-described embodiments.

In this context, a "fluidic connection" is understood to be a connection that permits the transportation of fluid between the fluidically connected components. For example, the fluid from the sampling site or the sample recipient vessel can be transported via the first fluid flow path to the chamber. For example, fluid from the gas reservoir can be transported via the second fluid flow path to the chamber.

The pump can be connected to the second fluid flow path in order to transport fluid from the gas reservoir into the chamber.

The pump can be designed as a piston pump that comprises a cylinder and a piston which can move therein that closes the cylinder fluid-tight on one side, wherein a chamber enclosed by the cylinder and the piston communicates with the first fluid flow path and the second fluid flow path.

The chamber can, for example, be a measuring cell chamber of a measuring cell of the analyzer. The valve can be an electrically actuatable valve, and the measuring and control electronics can be connected by electrical lines to the valve in order to actuate it. Likewise, the first and second valve device can be an electrically actuatable valve or components of another pump, or a valve block comprising a plurality of valves, wherein the measuring and control electronics are connected to the first and second valve device in order to actuate or control it. The pump can comprise a pump drive that can be controlled by the measuring and control electronics.

Another fluid line serving as a pressure compensation line can end in the chamber.

The chamber can be a measuring cell chamber of the analyzer. In this embodiment, the analyzer can comprise a measuring transducer that is arranged in or on the measuring cell to detect a measurand correlated with a parameter of a liquid sample to be determined of a reaction mixture formed from a liquid sample and at least one reagent and contained in the measuring cell chamber, and that is designed to generate an electrical measuring signal dependent upon the measurand, and that is connected to the measuring and control electronics so as to transmit the measuring signal. The measuring and control electronics can comprise a memory in which a calibration function or table is saved that assigns the measured values of the measurand to values of the parameter of the liquid sample to be determined. They can be programmed to receive a current measured value of the measuring sensor and ascertain and display or output a parameter value using the saved calibration function or table.

The analyzer can, moreover, comprise at least one pump that is fluidically connected to the first fluid line and comprises a pump drive that is connected to the measuring and control electronics, wherein the measuring and control electronics are designed to control the pump drive. By means of the pump, liquid can be introduced through the first fluid line into the chamber, or drawn out of the chamber.

BRIEF DESCRIPTION OF THE DRAWINGS

In the following, the invention is explained in further detail on the basis of an exemplary embodiment shown in the FIGURE:

FIG. 1 shows a schematic representation of an automated analyzer according to the present disclosure.

DETAILED DESCRIPTION

The schematically portrayed analyzer 1 in FIG. 1 is embodied to determine a parameter of a sample liquid 3 in a sample recipient vessel 2, said parameter depending upon the concentration of at least one analyte in the sample liquid 3. The analyzer 1 can, for example, be designed as a cabinet device in which all components portrayed in FIG. 1 are collected in a cabinet possibly with the exception of the sample recipient vessel 2. The parameter can, for example, be a cumulative parameter such as the chemical oxygen demand (COD) or the total phosphorus (TP). A plurality of particles 4 is contained in the sample liquid 3. The sample liquid 3 can, in particular, be a liquid mixture, a multi-phase mixture such as a suspension, or an emulsion in particular, a liquid with a solid load. The sample recipient vessel 2 can, for example, be a container connected to a sampling site of a process to be monitored, in which the sample liquid 3 is transported by means of a pump (not shown) from the sampling site. In an alternative exemplary embodiment, the analyzer 1 can be designed without a sample recipient vessel. In this embodiment, the sample liquid 3 is taken directly from a sampling site of a process, such as from a process vessel like a tube, fermenter, or basin, and analyzed by means of the analyzer 1, without being intermediately stored in the sample recipient vessel.

The analyzer 1 has a plurality of containers 5, 6, 7, 8, 9 that contain reagents to be added to the sample liquid 3 for determining the parameter and standard solutions for calibrating and/or adjusting the analyzer 1. Moreover, the analyzer 1 contains a measuring cell 10, a photometric measuring sensor 11, and a metering device 12. In addition, the analyzer 1 comprises a plurality of fluid lines which, in the present example, are designed as hose lines consisting of a flexible plastic material. The hose diameter is advantageously in the millimeter range, such as 1.6 mm, so that only slight amounts of sample liquid 3 and other reagents are needed in each case for an analytical cycle, i.e., for determining an individual value of the parameter. The analyzer 1 comprises a first pump 13 and a second pump 14 for transporting fluids through the fluid lines. To control the automated analyzer 1 and ascertain values of the parameter to be determined, the analyzer 1 has measuring and control electronics 15. The measuring and control electronics 15 can, for example, comprise a computer, microcomputer, measuring transducer, or other data processing device with one or more processors and one or more data memories. The analyzer 1 also comprises a central valve block 16 that contains a plurality of valves.

A first fluid line 17, connected via the valve block 16 to the metering device 12, has one end in the sample recipient vessel 2. The second pump 14 is designed as a peristaltic pump in the present example that comprises electrically driven pump mechanics which act from the outside to deform the fluid line 17 and thereby transport liquid through the fluid line 17. The metering device 12 comprises a metering vessel in this case, designed as a glass tube that encloses a metering chamber 18 in this case, the volume of the glass tube. The first pump 13 communicates with the metering chamber 18. In the present example, this is designed as a piston pump that comprises a cylinder, which communicates with the metering chamber 18, and a piston that moves therein and seals the cylinder liquid-tight at the rear. The piston movement is driven by means of a linear motor (not shown in FIG. 1). The measuring and control electronics 15 are connected to the drives of the first 13 and second pumps 14 by electrical lines, so that they can control the pumps 13, 14 according to an operating program saved in a memory of the measuring and control electronics 15.

The metering chamber 18 and the first pump 13 communicate with a gas line 19, by means of which the first pump 13 can draw air from the environment 28. The gas line 19 contains a valve 20 that in an open state permits, and in a closed state blocks, the transport of gas through the gas line 19.

The metering chamber 18 communicates with the first fluid line 17 via the valve block 16. Likewise, it communicates via the valve block 16 with other fluid lines 21, 22, 23, 24, and 25 which end in the fluid containers 5, 6, 7, 8, 9. Moreover, the metering chamber 18 communicates with a waste container (not shown in FIG. 1) via a valve 26 and a drain 27.

The valve block 16 comprises a plurality of valves that in an open state permit, or in a closed state correspondingly block, the transport of liquids, in particular, the reagents or standard solutions from the containers 5, 6, 7, 8, 9, or the transport of liquids from the metering chamber 18 into the drain 27. The valve block 16 and the valve 26 are connected to the measuring and control electronics 15, which are designed to actuate the valves of the valve block 16 and the valve 26 in order to convey liquids from the containers 5, 6, 7, 8, 9 according to a given drainage program, or to drain used liquid from the metering chamber 18 or measuring cell 10.

A plurality of detectors 30, 31 are arranged at different heights of the housing along the wall of the housing surrounding the metering chamber 18 in this case, the aforementioned glass tube. The detectors 30, 31 are designed to generate and output an electrical signal to the measuring and control electronics 15 when a liquid in the metering chamber 18 exceeds a fill level established by the position of the respective detector. The detectors 30, 31 in the present example are designed as light barriers and connected by electrical lines to the measuring and control electronics 15. Using the detector signals output by the detectors, the measuring and control electronics 15 can control the first 13 or second pump 14 to dose a specific liquid volume by setting a specific fill level in the metering chamber 18.

In the present example, the measuring cell 10 is made of a glass that is transparent to visible light and encloses a measuring cell chamber 37 which, on the one hand, communicates with the metering chamber 18 via a fluid line 32 ending in the measuring cell chamber 37 and, on the other hand, communicates with the surroundings 28 via a pressure compensation line 33 ending in the measuring cell chamber 37. A valve 34 is arranged in the fluid line 32 that in an open state permits, and in a closed state blocks, the transport of liquid or gas from the metering chamber 18 into the measuring cell chamber 37, or in the opposite direction. A valve 39 is also arranged in the pressure compensation line 33 that in an open state permits, and in a closed state blocks, a transport of fluid through the pressure compensation line 33.

The photometric measuring sensor 11 comprises a radiation source 35, which is designed to emit measuring radiation at one or more given wavelengths, and a radiation detector 36, which is designed to receive the measuring radiation and generate an electrical measuring signal that depends upon the intensity of the received measuring radiation. The wavelength or wavelengths of the measuring radiation are adapted to the parameter to be determined, or to the detection method used to determine the parameter, so that the extinction or absorption of the used measuring radiation in a reaction mixture formed during the detection method is a measure of the value of the parameter in the sample liquid 3. The radiation source 35 can, for example, comprise one or more light-emitting diodes, and the radiation detector 36 can comprise one or more photoelectric elements such as one or more photodiodes. The radiation source 35 and the radiation detector 36 are arranged on opposite sides of the measuring cell 10 so that measuring radiation emitted by the radiation source 35 along an optical path running through the measuring chamber 37 reaches the detector 36. The light intensity striking the detector 36 accordingly depends upon the extinction or absorption of a liquid or liquid mixture contained in the measuring cell reactor 37. A sensor circuit, which is not explicitly depicted, amplifies and/or digitizes, if applicable, the electrical signal from the detector 36. The measuring and control electronics 15 are designed, on the one hand, to control the radiation source 35 for emitting measuring radiation. On the other hand, the measuring and control electronics 15 are designed to receive and further process the signals from the detector 36. The further processing comprises, in particular, the ascertainment of values of the parameter to be determined using the signals from the detector 36.

The analyzer 1 shown in FIG. 1 can be operated to detect values of a parameter of the sample liquid 3 controlled by the measuring and control electronics 15 according to the method which follows. The measuring and control electronics 15 control the pumps 13, 14, as well as all valves and the measuring sensor 11 of the analyzer 1, and acquire signals from the detectors 30, 31, as well as measuring signals from the measuring sensor 11.

In a first step, a sample liquid 3 is conveyed by the second pump 14 via the fluid line 17 into the metering chamber 18, during which the valve 20 is opened. By means of the detectors 30, 31, a given volume of the sample liquid 3 is measured out of the sample liquid serving as a sample for measuring. For this purpose, the measuring and control electronics 15 control a pump drive of the second pump 14 using the detector signals from the detectors 30, 31. During this time, the valve 34, as well as the valves of the valve block 16 and the valve 26, are closed.

In a second step, the volume of the sample liquid 3 measured out in the metering chamber 18 is transported by the first pump 13 via the fluid line 32 into the measuring cell chamber 37. During this time, the valves 34 and 39 are open and the valve 20, the valves of the valve block 16 and the valve 26 are closed. The second pump 14 is not operated during this second step and, in this idle state, blocks transportation of sample liquid 3 through the fluid line 17 back into the sample recipient vessel 2. In the idle state, the pump 14 also functions like the valve device blocking the fluid line 17.

In another step, reagents are transported sequentially by the first pump 13 out of the containers 5, 6, 7 via the fluid lines 21, 22, 23 and the valve block 16 into the metering chamber 18, where a given volume of the reagents is measured by means of the detectors 30, 31 and transported further via the fluid line 32 into the measuring cell chamber 37. While a reagent is being transported from one of the containers 5, 6, 7 into the metering chamber 18, the valve of the valve block 16 arranged in the fluid flow path running from the desired container to the metering chamber 18 is open, and all other valves of the valve block 16 are closed. At the same time, the valves 26, 20 and 34 are closed. While the volume of a reagent measured in the metering chamber 18 is being transported into the measuring cell chamber 37, the second pump 14 is in the idle state; at the same time, the valves of the valve block 16 and valves 26 and 20 are closed, whereas the valves 34 and 39 are open.

While metering the sample liquid 3 and/or reagents, it is possible to repeatedly measure out a given volume of the sample liquid 3, or one or more reagents in the metering chamber 18, and transfer said volume to the measuring cell chamber 37, in order to meter larger volumes into the measuring cell chamber 37.

A reaction mixture is, accordingly, formed in the measuring cell chamber 37 from the reagents and the sample liquid 3, such that a chemical reaction occurs between one or more of the substances influencing the parameters to be determined and the reagents, which leads to either a consumption or formation of, for example, a colored substance. The reaction can, for example, comprise a chemical digestion of the substances. In an alternative embodiment, the reaction or digestion can also be first carried out in a reactor chamber that is spatially separate from the measuring cell 10 and fluidly connected to the measuring cell chamber 37, and, after the reaction has concluded, the reaction mixture can be transferred to the measuring cell chamber 37.

The measuring radiation of the measuring sensor 11 is chosen so as to comprise at least one wavelength that is absorbed by the, for example, colored substance formed in the chemical reaction. The absorption of the measuring radiation by the substance influences the intensity detected by the detector 36. The signal generated by the detector 36 and output to the measuring and control electronics 15 is, according to the Beer-Lambert law, a measure of the concentration of the substance, which in turn is a measure of the analyte concentration in the sample. Using a calibration function or calibration table saved in the measuring and control electronics 15, the measuring and control electronics 15 can ascertain a measured value of the parameter to be determined from the signal of the detector. This measured value is output through a user interface, or through an interface to a higher-level unit.

After ascertaining the measured value, the consumed reaction mixture can be drained from the measuring cell chamber 37 by first conducting at least part of the reaction mixture with the first pump 13 via the fluid line 32 back into the metering chamber 18. During this time, the valves 39 and 34 are open, the valves of the valve block 16 and valves 20 and 26 are closed, and the second pump 14 is in an idle state. Then, the consumed reaction mixture is drained out of the metering chamber 18 through the drain 27, during which the valves 34, 20 and the valves of the valve block 16 are closed, and a second pump 14 is an idle state. These steps can be repeated as needed, until the measuring cell chamber 37 is completely drained.

The above-described steps form a measuring cycle of the analyzer 1. Such measuring cycles can be repeatedly performed. Between each two measuring cycles, rinsing and/or calibration or adjustment cycles can be performed. During a calibration or adjustment cycle, the process is basically the same as described above with regard to a measuring cycle; however, a calibration standard is transported from one of the containers 8, 9 into the measuring cell chamber, instead of the sample liquid 3. By comparing the value of the parameter known for the calibration standard with the value of the parameter currently ascertained for the calibration standard in the calibration or adjustment cycle, the measuring and control electronics 15 can perform a calibration and/or adjustment of the analyzer 1.

In a rinsing cycle, the sample liquid 3, including its particle load 4, is transported by the second pump 14 from the sample recipient vessel 2 via the fluid line 17 into the metering chamber 18. At the same time, the valves of the valve block 16, as well as the valves 26 and 34, are closed, and the valve 20 is open. Then, the sample liquid 3 is transported by the first pump 13 from the metering chamber 18 via the fluid line 32 into the measuring cell chamber 37. At the same time, the valves 20, 26 and the valves of the valve block 16 are closed, and the valves 34 and 33 are open. During this time, the second pump 14 is in an idle state. The steps of conveying the sample liquid 3 into the metering chamber 18, and subsequently conveying the sample liquid 3 out of the metering chamber into the measuring cell chamber 37, can be repeated several times in order to convey a larger rinsing volume into the measuring cell chamber 37.

Then, the sample liquid 3 is transported out of the measuring cell chamber 37 back into the metering chamber 18, and, from there, via the drain 27 into a waste container. This can also be repeated several times, to drain the measuring cell chamber 37 in steps when there are large rinsing volumes.

As described at the onset, particles 4 contained in the sample liquid used for rinsing may cause a blockage of, in particular, the valve 34, but also possibly other valves of the valve block 16 or the valve 26. The valve 34 may be especially at risk, since the sample liquid 3 can remain for a long time in the measuring cell chamber 37 particularly when a large rinsing volume is metered stepwise into the measuring cell chamber 37. Particles 4 in the sample liquid 37 can settle during this time period. While the sample liquid 3 is being drained from the measuring cell chamber 37, the settled particles 4 enter the narrow sections, such as the valve seat of the valve 34, all at once, which can cause this valve 34 to quickly become blocked.

A similar effect can occur when particles 4 remain in the reaction mixture consumed after a measuring cycle.

If an error (i.e., fault) occurs during a measuring, rinsing, or calibration or adjustment cycle of the analyzer 1, the measuring and control electronics 15 stop the operation of the analyzer and completely drain the measuring cell chamber 37 through the metering chamber 18. If particles 4 are in the liquid contained in the measuring cell chamber 18 at this point in time, such a blockage, in particular of the valve 34, can also occur.

In order to prevent this error, the measuring and control electronics 15 can control the analyzer 1 so as to drain the measuring cell chamber 37 during a measuring cycle, rinsing cycle, or, in the event of a fault, according to the operating method described below. For this purpose, a corresponding computer program is saved in a memory of the measuring and control electronics 15 that is executed by the measuring and control electronics 15.

In a first step of this method, the first pump 13 draws air from the surroundings 28 through the fluid line 19 and the open valve 20. At the same time, the second pump 14 is in an idle state, and the valves of the valve block 16 and the valves 26 and 34 are open.

In a second step, the pump 13 then transports the drawn air via the metering chamber 18 through the fluid line 32 and the open valve 34 into the measuring cell chamber 37. At the same time, the second pump 14 is idling, the valves of the valve block 16, the valve 26 and the valve 20 are closed, and the valve 39 is open. The drive of the pump 13 can be simultaneously controlled by the measuring and control electronics 15 so as to move the piston of the pump 13 at a speed such that the air enters the measuring cell chamber 37 in bursts. The gas volume drawn and transported into the measuring cell chamber 37 in the first and second steps may be much larger than the inner volume of the fluid line 32, so that liquid which remains in the fluid line 32 is forced back into the measuring cell chamber 37 while the air is being transported into the measuring cell chamber 37 and, in addition, a sufficient volume of gas enters the measuring cell chamber 37.

The first and second steps can be repeated several times. During this time, particles 4 that have settled in the measuring cell chamber 37 are stirred up in the liquid in the measuring cell chamber 37, which can, for example, be the pure sample liquid 3 used as rinsing liquid, or a reaction mixture consisting of the sample liquid 3 and the reagents.

In a third step, immediately after the particles 4 have been stirred up, at least part of the liquid in the measuring cell chamber 37 is drawn by the first pump 13 out of the measuring cell chamber 37 through the fluid line 32 and the open valve 34, and transported into the metering chamber 18. At the same time, the valve 39 is open, the valves of the valve block 16 and valves 26 and 20 are closed, and the second pump 14 is in an idle state. Drawing can occur abruptly in that the first pump 13 sequentially draws, with brief interruptions, small volumetric units from the measuring cell chamber 37 of the overall volume of liquid to be drained from the measuring cell chamber 37 in the third step. During this time, the delivery speed with which the first pump 13 transports the liquid, or a part of the liquid, or possibly the individual small volumetric units, out of the measuring cell chamber into the metering chamber 18 is significantly faster than the delivery speed at which it transports liquids into the measuring cell chamber 37 in a measuring or rinsing cycle, e.g., 2 to 10 times as fast.

In a fourth step directly following the third step, the liquid is drained by the first pump 13 from the metering chamber 18 through the drain 27. During this time, the valves of the valve block 16 and the valves 20 and 34 are closed, the valve 26 is open, and a second pump 14 is in an idle state.

The third and fourth steps can be repeated as needed until the measuring cell chamber 37 is completely drained. If needed, the first and second steps can be performed once or several times in order to again stir up the particles after performing the third and fourth steps once or several times.

Stirring up and drawing off the particles 4 possibly, abruptly counteracts an even liquid flow through the fluid line 32 and the valve 34, and causes the particles 4 to pass through the narrow sections of the valves in a jumbled manner and not all at once. This effectively counteracts blockage.

The invention claimed is:

1. An analyzer for determining a parameter value of a liquid, the analyzer comprising:
   measuring and control electronics;
   a chamber embodied as a measuring cell chamber and/or a reactor chamber;
   a fluid line connected to the chamber, including a valve arranged in the fluid line and configured to enable transport of a gas or a liquid in an open state and to prevent the transport of the gas or the liquid in a closed state;
   a first fluid flow path including a first valve device structured to selectively block or open the first fluid flow path, the first valve device fluidically connecting a sampling site or a sample recipient vessel to the chamber;
   a pump arranged in the first fluid flow path; and
   a second fluid flow path including a second valve device structured to selectively block or open the second fluid flow path, and the second valve device fluidically connecting the chamber to a gas reservoir,
   wherein the measuring and control electronics are configured to control the analyzer, including the pump, valve, first valve device and second valve device, to:
   transport a first volume of a liquid containing a plurality of particles into the chamber along the first fluid flow path using the pump;
   transport at least one reagent into the chamber;
   detect at least one measured value of a measurand of a reaction mixture formed in the chamber from the first volume of the liquid and the at least one reagent, the measurand correlated to a parameter value of the liquid;
   drain the reaction mixture from the chamber through the fluid line and through the valve arranged in the fluid line, wherein the valve is configured to selectively block and enable fluid transport through the fluid line to and from the chamber;
   subsequently transport a second volume of the liquid containing a plurality of particles into the chamber via the fluid line, the second volume taken from a same source as the first volume;
   introduce a gas or gas mixture from the gas reservoir along the second fluid flow path and through the fluid line via the valve into the chamber and through the liquid present in the chamber such that the particles in the liquid are stirred up and dislodged from an opening of the fluid line into the chamber; and
   drain at least a portion of the liquid from the chamber through the fluid line and through the valve arranged in the fluid line,
   wherein the fluid line, via which the liquid is drained from the chamber, is further used for the transporting of the liquid containing the plurality of particles into the chamber, and wherein both the first fluid flow path and the second fluid flow path include the fluid line and the valve.

2. The analyzer according to claim 1, wherein the fluid line ends in the chamber.

3. The analyzer according to claim 1, wherein the gas reservoir is the atmosphere surrounding the analyzer.

4. A method for operating an automated analyzer using an analyzer according to claim 1, comprising:
   providing the analyzer of claim 1;
   transporting the first volume of the sample liquid containing a plurality of particles into the chamber via the fluid line;
   transporting the at least one reagent into the chamber via the fluid line;

detecting the at least one measured value of the measurand of the reaction mixture formed in the chamber from the first volume of the sample liquid and the at least one reagent;

draining the reaction mixture from the chamber through the fluid line and through the valve arranged in the fluid line;

subsequently transporting the second volume of the sample liquid containing a plurality of particles into the chamber via the fluid line;

introducing the gas or gas mixture through the fluid line via the valve into the chamber and through the second volume of the sample liquid present in the chamber such that the particles in the second volume of the sample liquid are stirred up and dislodged from an opening of the fluid line into the chamber; and draining at least a portion of the second volume of the sample liquid from the chamber through the fluid line and through the valve.

5. The method according to claim 4, further comprising: ascertaining the parameter value using the detected at least one measured value.

6. The method according to claim 4, further comprising repeating the steps of introducing the gas or gas mixture and subsequently draining at least a portion of the second volume of the sample liquid from the chamber once or several times until the chamber is at least substantially drained.

7. The method according to claim 4, wherein the gas or gas mixture is introduced in bursts.

8. The method according to claim 4, wherein the sample liquid is transported into the chamber at a first delivery rate, and wherein at least a portion of the sample liquid is drained at a second delivery rate that is faster than the first delivery rate.

9. The method according to claim 4, wherein the draining of at least a portion of the reaction mixture and/or the sample liquid includes drawing a portion of the liquid using a pump, and wherein the drawing is interrupted at least once.

10. The method according to claim 4, wherein the gas or gas mixture is introduced into the chamber from a gas reservoir under pressure via a fluid flow path connected to the chamber, the fluid flow path including the fluid line and the valve.

11. The method according to claim 4, wherein the gas or gas mixture is air, and wherein the air is drawn using an analyzer pump from the atmosphere surrounding the analyzer and is introduced into the chamber using the analyzer pump via a fluid flow path including the fluid line and the valve.

12. The method according to claim 4, wherein the chamber is a reactor chamber.

13. The method according to claim 4, wherein the steps of the method are automated using the measuring and control electronics.

14. The method according to claim 4, wherein the chamber is a measuring cell chamber.

15. The method according to claim 4, wherein the chamber is a reactor and measuring cell chamber.

* * * * *